(12) United States Patent
Steadman Booker et al.

(10) Patent No.: US 10,725,188 B2
(45) Date of Patent: Jul. 28, 2020

(54) POLARIZATION CORRECTION FOR DIRECT CONVERSION X-RAY DETECTORS

(71) Applicant: KONINKLIJKE PHILIPS N.V., Eindhoven (NL)

(72) Inventors: Roger Steadman Booker, Aachen (DE); Ewald Roessl, Ellerau (DE); Heiner Daerr, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 123 days.

(21) Appl. No.: 15/762,160

(22) PCT Filed: Oct. 11, 2016

(86) PCT No.: PCT/EP2016/074325
§ 371 (c)(1),
(2) Date: Mar. 22, 2018

(87) PCT Pub. No.: WO2017/067817
PCT Pub. Date: Apr. 27, 2017

(65) Prior Publication Data
US 2018/0284303 A1 Oct. 4, 2018

(30) Foreign Application Priority Data
Oct. 20, 2015 (EP) .................................... 15190530

(51) Int. Cl.
*G01T 7/00* (2006.01)
*G01T 1/24* (2006.01)
*A61B 6/00* (2006.01)

(52) U.S. Cl.
CPC ................. *G01T 7/005* (2013.01); *G01T 1/24* (2013.01); *G01T 1/247* (2013.01); *A61B 6/4241* (2013.01); *A61B 6/585* (2013.01)

(58) Field of Classification Search
CPC ....... G01T 7/005; G01T 1/247; A61B 6/4241; A61B 6/585
(Continued)

(56) References Cited

U.S. PATENT DOCUMENTS 7,652,258 B2   1/2010  Shahar
2009/0128216 A1   5/2009  Rao
(Continued)

FOREIGN PATENT DOCUMENTS

EP         0224351        6/1987
WO     WO-2013061186 A1 *  5/2013
(Continued)

*Primary Examiner* — Kenneth J Malkowski
(74) *Attorney, Agent, or Firm* — Larry Liberchuk

(57) ABSTRACT

Photon-counting x-ray detectors (3) suffer from a degradation of their performance due to polarization. In order to correct the effects of polarization to the generated x-ray images, the invention suggests (i) exposing the radiation detector (3) to a first radiation pulse emitted by a further radiation source (11) and obtaining a first electric pulse signal generated by the radiation detector (3) in response thereto, (ii) later exposing the 5 radiation detector (3) to a second radiation pulse emitted by the further radiation source (11) during the acquisition of the image and obtaining a second electric pulse signal generated by the radiation detector (3) in response thereto, and (iii) comparing amplitudes of the first and second electric pulse signals and generating the x-ray image based on a result of the comparison. The invention provides a corresponding x-ray device and a corresponding method.

15 Claims, 4 Drawing Sheets

(58) Field of Classification Search
USPC .......................................................... 378/207
See application file for complete search history.

(56) References Cited

U.S. PATENT DOCUMENTS

| | | |
|---|---|---|
| 2010/0078558 A1 | 4/2010 | Prokesch |
| 2011/0253886 A1 | 10/2011 | Hackenschmied |
| 2013/0108019 A1 | 5/2013 | Tkaczyk |
| 2014/0140469 A1 | 5/2014 | Carmi |

FOREIGN PATENT DOCUMENTS

| | | |
|---|---|---|
| WO | 2013/174141 | 11/2013 |
| WO | 2014072939 | 5/2014 |
| WO | 2014132232 | 9/2014 |
| WO | 2016091981 | 6/2016 |
| WO | 2017046002 | 3/2017 |

* cited by examiner

POLARIZATION CORRECTION FOR DIRECT CONVERSION X-RAY DETECTORS

CROSS REFERENCE TO RELATED APPLICATIONS

This application is the U.S. National Phase application under 35 U.S.C. § 371 of International Application No. PCT/EP2016/074325, filed Oct. 11, 2016, published as WO 2017/067817 on Apr. 27, 2017, which claims the benefit of European Patent Application Number 15190530.4 filed Oct. 20, 2015. These applications are hereby incorporated by reference herein.

FIELD OF THE INVENTION

The invention generally relates to spectral x-ray imaging. More specifically, the invention relates to an x-ray device for generating an x-ray image of an object comprising a spectral radiation detector and to a method for generating an x-ray image of an object using a spectral radiation detector.

BACKGROUND OF THE INVENTION

In so-called spectral or photon-counting x-ray imaging, x-ray photons incident onto the radiation detector of the x-ray device can be detected individually and their energies can be determined. For this purpose the radiation detector comprises a direct conversion material, such as, for example, cadmium telluride (CdTe) or cadmium zinc telluride (CZT), which produces a pulse-like current signal when a photon enters the material, where the current pulse corresponds to an amount of charge which is indicative of the photon energy. In order to determine the photon energy, the radiation detector generates an electric pulse signal representing the amount of charge generated by an x-ray photon, and the amplitude of this electric pulse signal is allocated to one of plural predetermined energy ranges, which are usually also referred to as energy bins. During an x-ray scan, the numbers of photons allocated to the energy bin are counted, and the x-ray image is reconstructed on the basis of the count numbers. In so doing, x-ray images may be reconstructed which may comprise one sub-image for each energy range and/or which show a material composition of the object with respect to different materials of interest.

A known problem of the direct conversion radiation detectors used in spectral x-ray imaging is their instability resulting from trapped charges. Such charges modify the electric field within the radiation detector and thereby cause a degradation of the charge collecting properties of the detector. This degradation is usually referred to as polarization. As a result of the polarization effect, the amount of charge produced by the material at a given energy of the x-ray photons may change with time and/or photon flux. This may lead to an incorrect assessment of the photon energies, which may result in artifacts in the reconstructed x-ray images.

US 2014/0140469 discloses a computed tomography (CT) device comprising a primary x-ray source and an x-ray detector which produces a signal current in proportion to the total energy of the photons absorbed by the detector. In this regard, the x-ray detector has an unstable gain and the CT device is configured to perform a gain calibration procedure. For this purpose, the CT device comprises a supplemental x-ray source which is used to illuminate the x-ray detector in several supplemental scans. On the basis of the detector signals measured in the supplemental scans, calibration data are determined which is used to correct the signal of the object scan.

SUMMARY OF THE INVENTION

It is an object of the present invention to reduce artifacts in x-ray images, which result from a polarization of the radiation detector.

In a first aspect of the invention, an x-ray device for generating an x-ray image of an object is suggested. The device comprises a spectral radiation detector and an x-ray radiation source, the radiation detector converting x-ray radiation emitted by the x-ray radiation source and having traversed the object into electric pulse signals corresponding to x-ray photon events during acquisition of the image. The device comprises a further radiation source configured to expose the radiation detector to a first radiation pulse and configured to expose the radiation detector to a second radiation pulse during the acquisition of the x-ray image, the first and second radiation pulse being emitted in accordance with the same configuration of the further radiation source. Moreover, the device comprises a detection circuit configured to detect a first electric pulse signal generated by the radiation detector due to the exposure of the radiation detector to the first radiation pulse and configured to detect a second electric pulse signal generated by the radiation detector due to the exposure of the radiation detector to the second radiation pulse. Furthermore, the x-ray device is configured to compare amplitudes of the first and second electric pulse signals and to generate the x-ray image based on a result of the comparison.

Since the first and second radiation pulses are emitted in accordance with the same configuration of the further radiation source (e.g. with respect to the intensity, wavelength and/or pulse duration), the electric pulse signals generated by the radiation detector in response to the exposure to the first and second radiation pulses would correspond to each other, when the radiation detector was not affected by polarization. By comparing the electric pulse signals generated by the radiation detector in response to the exposure to the first and second radiation pulses, it is therefore possible to assess the polarization of the radiation detector, and by generating the x-ray image on the basis of the result of this comparison, it is possible to correct the effects of the polarization and/or compensate for such effects. Hereby, image artifacts resulting from detector polarization can be reduced.

By exposing the radiation detector to each of the first and second radiation pulse an x-ray photon event is particularly generated or simulated. Correspondingly, each of the first and second electric pulse signals particularly corresponds to an electric pulse signal generated by the radiation detector in response to an incident x-ray photon having a certain energy.

In one embodiment, the further radiation source is a laser device and the first and second radiation pulses comprise laser radiation. However, is likewise possible to use other types of radiation sources, such as, for example, LED light sources and radioactive radiation sources.

While the radiation detector is exposed to the second radiation pulse during the acquisition of the x-ray image in order to assess the effect of a possible detector polarization on the image acquisition, the further radiation source may be controllable to expose the radiation detector to the first radiation pulse prior to or at the beginning of the acquisition of the image. Thus, the first electric pulse signal generated in response to the exposure of the radiation detector to the first radiation pulse may serve as a reference signal, which reflects the charge collection properties of the radiation detector prior to or at the beginning of the image acquisition. These properties usually correspond to the charge collection properties on the basis of which the energy calibration of the radiation detector (i.e. the allocation between amplitudes of electric pulse signals generated in response to detected x-ray photons and energy ranges or bins) is made. Hence, the generation of the x-ray image on the basis of the result of the comparison of the amplitudes of the first and second electric pulse signals allows for correcting or compensating for changes of the charge collection properties of the detector compared with the properties at the time of the energy calibration.

Since at least the second radiation pulse is received in the radiation detector during image acquisition and, thus, while x-ray radiation is generally also incident onto the radiation detector, the second radiation pulse is preferably emitted in such a manner that the electric pulse signal generated by the radiation detector in response to the exposure to the second radiation pulse can be distinguished from electric pulse signals generated in response to incident x-ray radiation.

In this respect, one embodiment of the invention includes that the configuration of the further radiation source is selectable such that an amplitude of the first and second electric pulse signals is higher than amplitudes of electric pulse signals generated by the radiation detector in response to an exposure to x-ray radiation and that the detection circuit is configured to identify an electric pulse signal generated by the radiation detector, which has the highest amplitude during an acquisition period, as the second electric pulse signal. The acquisition period may particularly correspond to a predetermined time period during the acquisition of the x-ray image, in which the further radiation source emits one second radiation pulse. When a computed tomography (CT) scan is carried out, the acquisition period may particularly correspond to one or plural frames, where in each frame one projection is measured. In a further embodiment, the further radiation source is controllable to expose the radiation detector to the first and/or second radiation pulses in a time period in which the emission of x-ray radiation by the x-ray radiation source is interrupted.

Further, the detection circuit may comprise a peak and hold circuit for determining the amplitude of the first and/or second electric pulse signals, where the peak and hold circuit may monitor a signal and hold its maximum. If the detector is exposed to the first and/or second radiation pulses in a time period in which the emission of x-ray radiation by the x-ray radiation source is interrupted, the peak and hold circuit may be controllable such that it is only activated while the x-ray radiation source does not emit x-ray radiation. This may particularly be the case when amplitudes of the first and second electric pulse signals are not higher than the amplitudes of the electric pulse signals generated by the radiation detector in response to incident x-ray radiation.

In one embodiment of the invention, the further radiation source is configured to expose the radiation detector to at least two first radiation pulses emitted in accordance with different configurations of the further radiation source and to at least two second radiation pulses, each second radiation pulse being emitted in accordance with one of said configurations of the further radiation source. For each second radiation pulse emitted in accordance with one of the configurations of the further radiation source, the x-ray device is configured to compare the electric pulse signal generated in response to the exposure of the radiation detector to the respective second radiation pulse with the electric pulse signal generated by the radiation detector in response to the exposure to the first radiation pulse emitted in accordance with the same configuration of the further radiation source, and the x-ray device is further configured to generate the x-ray image based on the results of the comparisons. By evaluating measurements for radiation pulses configured differently (e.g. having different intensities, wavelengths and/or durations) it is particularly possible to assess polarization on different points of the amplitude-height domain and to take account of variations of the influences of the polarization with the amplitude of the electric pulse signals generated in the radiation detector and/or with different energies of x-ray photons.

Particularly in case the detector is exposed to the first and/or second radiation pulses in a time period in which the emission of x-ray radiation by the x-ray radiation source is interrupted, the further radiation source may be controllable to successively emit at least two second radiation pulses in one a time period in which the emission of x-ray radiation by the x-ray radiation source is interrupted. This allows for evaluating the polarization effect for differently configured radiation pulses or different amplitudes of the second electric pulse signal essentially at the same time (and thus in the same stage of the polarization process). However, since polarization does usually build up on larger time scales, the at least two second radiation pulses can be generated in a certain time distance in further embodiments.

The generation of the x-ray image on the basis of the result of the comparison of the amplitudes of the first and second electric pulse signals may particularly comprise applying corrections in the process of reconstructing the x-ray image using measurement data provided by the radiation detector.

Therefore, one embodiment of the invention includes that the x-ray device comprises a reconstruction unit configured to reconstructs the x-ray image based on electric pulse signals generated by the radiation detector in response to an exposure to x-ray radiation and based on the result of the comparison between the amplitudes of the first and second electric pulse signals.

In a related embodiment, the radiation detector is configured to allocate an energy range to each of a plurality of x-ray photons entering the radiation detector based on the electric pulse signals generated in response to the entering of the x-ray photons and the reconstruction unit is configured to modifies the allocation for at least some of the x-ray photons based on the result of the comparison between the first and second electric pulse signals. In particular, the reconstruction unit may carry out the image reconstruction on the basis of shifted and/or scaled energy ranges.

In addition or as an alternative to the corrections applied in the process of reconstructing the x-ray image using the output of the radiation detector, the configuration of the radiation detector may be adapted to compensate for effects of a detector polarization. In this regard, one embodiment of the invention comprises that the x-ray device comprises read-out electronics of the radiation detector and that the read-out electronics are configured to process the electric pulse signals generated in response to an exposure to x-ray radiation based on the result of the comparison between the first and second electric pulse signals.

In one related embodiment of the invention, the processing of the electric pulse signals generated in response to an exposure to x-ray radiation includes amplifying the electric pulse signals using a gain selected on the basis of the result of the comparison between the first and second electric pulse signals. In a further related embodiment, the processing of the electric pulse signals generated in response to an exposure to x-ray radiation includes allocating energy ranges to the electric pulse signals based on the result of the comparison between the amplitudes of the first and second electric pulse signals. In a further aspect of the invention, a method for generating an x-ray image of an object using a photon-counting radiation detector is suggested, where the detector converts x-ray radiation emitted by an x-ray radiation source and having traversed the object into electric pulse signals corresponding to x-ray photon events during acquisition of the image. The method comprises:

exposing the radiation detector to a first radiation pulse emitted by a further radiation source in accordance with a configuration of the further radiation source and obtaining a first electric pulse signal generated by the radiation detector in response to the exposure to the first radiation pulse;

later exposing the radiation detector to a second radiation pulse emitted by the further radiation source in accordance with the same configuration of the further radiation source during the acquisition of the image and obtaining a second electric pulse signal generated by the radiation detector in response to the exposure to the second radiation pulse;

comparing amplitudes of the first and second electric pulse signals and generating the x-ray image based on a result of the comparison.

It shall be understood that the x-ray device of claim 1 and the method of claim 15 have similar and/or identical preferred embodiments, in particular as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
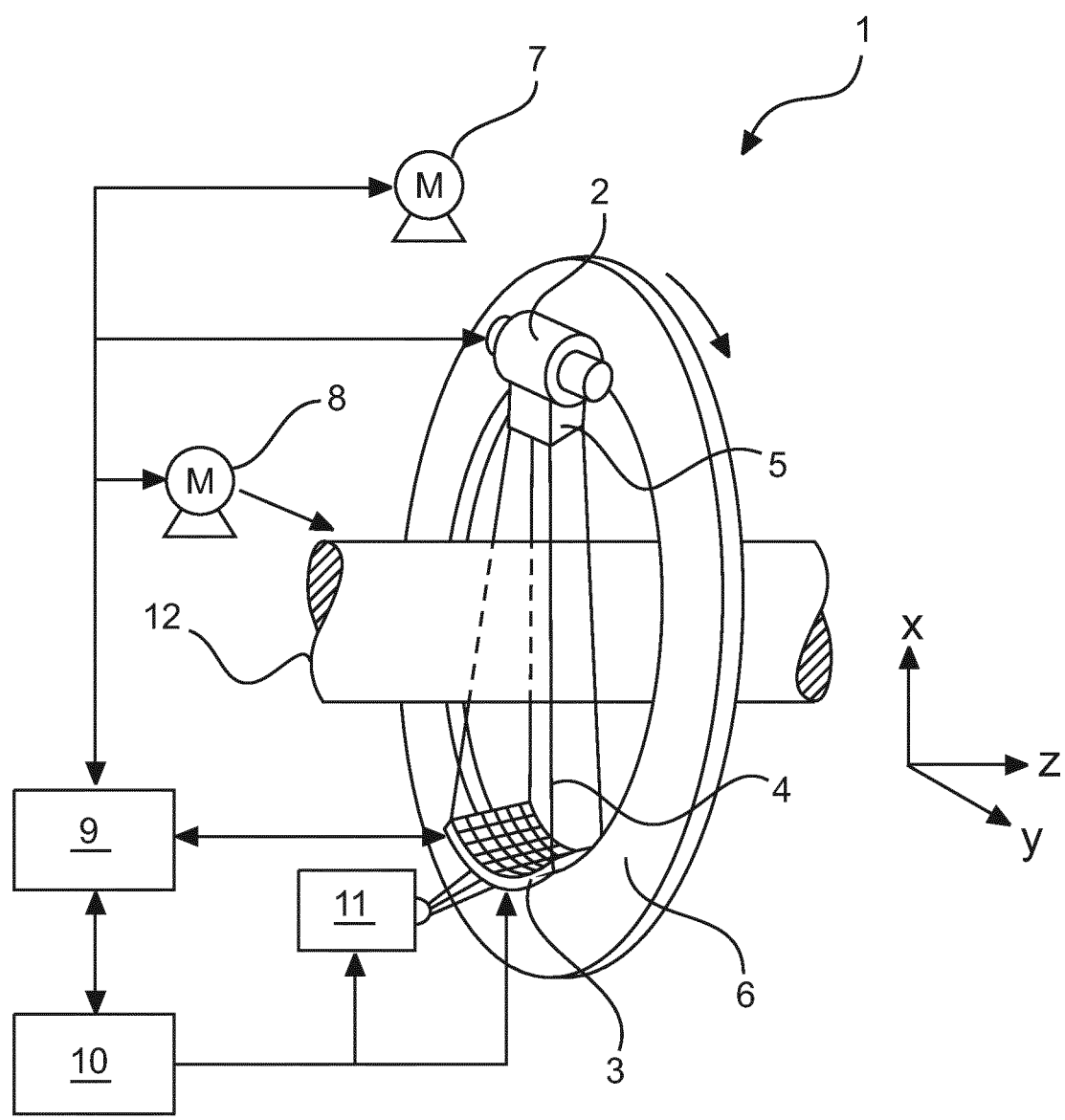
FIG. 1 schematically and exemplarily shows components of an x-ray device including one or more radiation source(s) for emitting test radiation pulses for assessing a polarization of a radiation detector of the x-ray device, FIG. 2 schematically and exemplarily shows a detector element of the radiation detector of the x-ray device and components of read-out electronics of the detector element, FIG. 3 schematically and exemplarily shows a radiation emitter for emitting test radiation pulses, which are directed to a detector element using beam splitters, FIG. 4 schematically and exemplarily shows electric pulse signals generated in a detector element in response to incident x-ray photons and an incident test radiation pulse and an output signal of a peak and hold circuit for determining the amplitude of the signal pulse resulting from the incident rest radiation pulse in one embodiment, FIG. 5 schematically and exemplarily shows electric pulse signals generated in a detector element in response to incident x-ray photons and an incident test radiation pulse and an output signal of a peak and hold circuit for determining the amplitude of the signal pulse resulting from the incident rest radiation pulse in a further embodiment, and FIG. 6 schematically and exemplarily shows electric pulse signals generated in a detector element in response to incident x-ray photons and an incident sequence of test radiation pulses.

FIG. 1 schematically and exemplarily illustrates components of an x-ray device 1 for imaging an object. In one embodiment, the x-ray device 1 may be a CT device for generating three-dimensional images of the object. However, the x-ray device 1 may likewise be configured in another way. The object to be imaged may be a human or animal body or any other object, the internal structure of which is to be imaged using the x-ray device 1.

The x-ray device 1 comprises an x-ray source 2, such as an x-ray tube, and a radiation detector 3. The x-ray source 2 produces an x-ray beam 4 which traverses an examination region 12 between the x-ray source 2 and the radiation detector 3 before x-ray radiation is collected by the radiation detector 3. For shaping the x-ray beam, the x-ray source 2 may be provided with a suitable collimator 5. The object is placed on a support (not shown in the figure) which can be positioned in the examination region 12. In case the object is a patient body, the support may be configured as a patient table.

In case the x-ray device 1 is configured as a CT device, the x-ray source 2 and the radiation detector 3 are mounted at opposing positions on a rotatable gantry 6 which is driven by a motor 7. By means of the motor 7, the gantry 6 can be rotated such that the x-ray source 2 and the radiation detector 3 can be rotated around an object to be imaged positioned within the examination region 12. Thus, different projections can be successively acquired, where each projection corresponds to one angular position of the x-ray source 2 and the radiation detector 3 relative to the object to be imaged. The period for acquiring one of these projections is also referred to as a frame herein. By moving the object and the gantry 6 relative to each other in the direction of the z-axis, i.e. perpendicular to the beam direction, different so-called slices of the object can be imaged. For this purpose, the support (and, thus, the object) may be displaced back and forth within the examination region 12 in the direction of the z-axis by means of a further motor 8. However, it is also possible that the support is not moved, but that the gantry 6 can be displaced in the direction of the z-axis.

The x-ray source 2 and (optionally) the radiation detector 3 are coupled to a control unit 9 controlling the operation of the x-ray source 2 and the radiation detector 3. With respect to the x-ray source 2, the control unit 9 particularly controls timing and power for generating x-ray radiation; control functions of the control unit 9 with respect to the radiation detector will be described further below. Moreover, the control unit 9 controls the motors 7 and 8 driving the gantry 6 and the object support.

The radiation detector 3 is further coupled to a reconstruction unit 10 which reconstructs images on the basis of the measurement data collected by the radiation detector 3. These measurement data are projections of the object, and images can be reconstructed from these projections in a way known to a person skilled in the art. Since an energy-discriminating photon-counting detector 3 is used which determines photon energies in accordance with predetermined energy ranges (as will be further explained herein below), the x-ray images generated in the x-ray device 1 may comprise a set of sub-images including one sub-image for each energy range and/or with respect to different materials of interest included in the imaged object (so-called material decomposition). These sub-images may also be combined to form one image for the plural energy ranges.

The control unit 9 and the reconstruction unit 10 may be configured as computer devices which comprise processor units to execute computer programs implementing the routines carried out by the control unit 9 and the reconstruction unit 10. In one embodiment, the control unit 9 and the reconstruction 10 are implemented in separate computer devices. However, it is likewise possible that the control unit 9 and the reconstruction unit 10 are included in a single computer device and implemented in several processor units or a single processor unit of the computer device.

The radiation detector 3 is configured as a photon-counting detector which is capable of detecting single incident x-ray photons and allows for determining their energies in accordance with a number of predefined energy bins. In this regard, a photon incident into the radiation detector 3 produces an electric charge cloud of charge carriers (electrons and holes) which drift to the detector electrodes, where the amount of charge depends on the energy of the incident x-ray photon. The generated charges are collected by read-out electronics of the radiation detector 3, which in turn generates an electrical signal (e.g. a voltage signal) the amplitude of which is proportional to the energy of the impinging x-ray photon.

More specifically, the radiation detector 3 may comprises a plurality of detector elements 201, which are sometimes also referred to as modules or tiles and which are preferably arranged in an array which may be flat or concave. Thus, the detector elements 201 are arranged in the form of rows and columns arranged perpendicular to each other. Components of such a detector element 201 are schematically and exemplarily depicted in FIG. 2.

In accordance with the illustrated configuration, each detector element 201 comprises a converter element 202 for converting X-rays into electrical signals, which element is provided between a cathode contact 203 and an anode contact assembly 204. The converter element 202 is made of a semiconductor material, where suitable semiconductor materials are, for example, cadmium telluride (CdTe), cadmium zinc telluride (CZT), cadmium tellurium selenide (CdTeSe), CdZnTeSe, cadmium manganese telluride (CdMnTe), silicon (Si), gallium arsenide (GaAs) and mercury iodide (HgI). The cathode contact 203 is generally held on a lower electric potential than the anode contact assembly 204 (i.e. a negative bias voltage is applied to the cathode contact 203 with respect to the anode contact assembly 204) so that an electric field is formed between the cathode contact 202 and the anode contact assembly 303 within the converter element 202. The cathode side of the converter element 202 may point towards the x-ray source 2 so that x-ray photons enter into the converter element 202 through the cathode contact 203 and so that the electric field is parallel to the (main) beam direction. However, it is likewise possible that the detector element 201 is configured in another way.

The converter element 202 may be configured as a substantially cubic block and its lateral dimensions may be much larger than its thickness. The cathode contact 203 and the anode contact assembly 204 may be connected to the large top and bottom sides of the converter element 202 so that the electric field extends along the smaller thickness direction of the converter element 202. Further, the cathode contact 203 may be configured as a continuous cathode electrode, which may be formed by a thin metalized film applied onto the converter element 202. In contrast, the anode assembly 204 may include pixelated anode electrodes 205, i.e. separated anode electrodes 205 which are arranged in certain distances to each other and which are usually also referred to as anode pixels. In one embodiment, these anode pixels 205 are also arranged in rows and columns, which are perpendicular to each other, on the surface of the conversion element 202.

The anode electrodes or pixels 205 collect charge produced by photons incident on the converter element 301 and each anode pixel is connected to readout electronics which collect the resulting current and determine the measurement data which are subsequently provided to the reconstruction unit 10. Thus, when an x-ray photon enters into the converter element 301, it excites the semiconductor material and thereby generates electric charge carriers (electrons and holes). The negative charge carriers drift to one of the anode electrodes 34 under the influence of the electric field in the converter element 301 and produce the aforementioned electric signal pulse collected by the read-out electronics, which may be implemented in a CMOS ASIC structure attached to the anode side of the converter element, for example.

Figure 2:
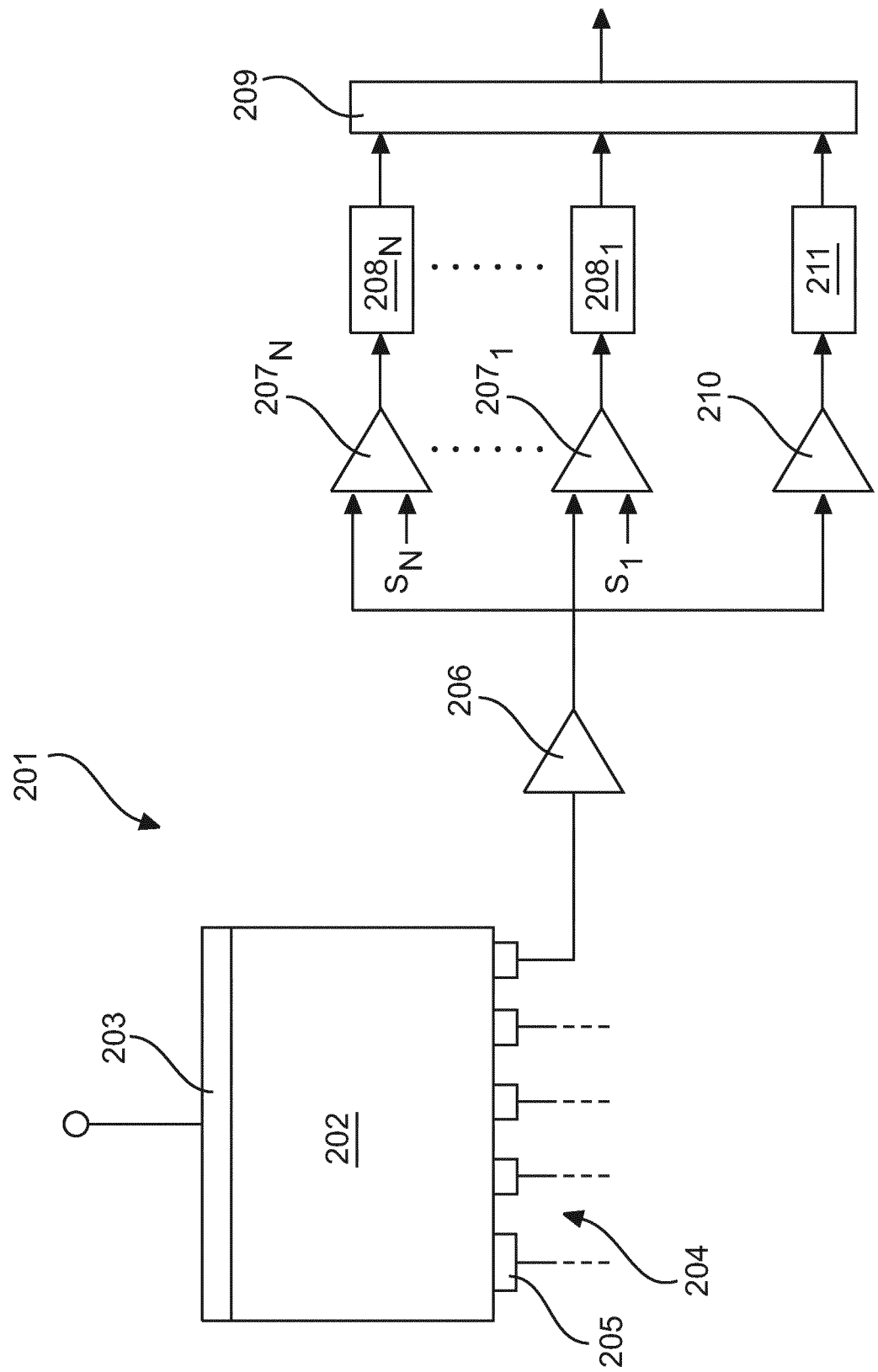

FIG. 2 also schematically and exemplarily illustrates components of the read-out electronics for one anode pixel 205 in one embodiment. In this embodiment, the read out electronics may particularly include an amplifier 206, such as a charge sensitive amplifier, which integrates the input current over each event (e.g. an incident x-ray photon) and produces a corresponding step-like output voltage signal. The amplifier signal is preferably filtered in a so-called pulse shaper circuit included in the amplifier 206 particularly in order to produce a pulse amplitude proportional to the step generated by the charge-sensing amplifier (i.e. to the integrated charge of the charge cloud generated by an incident x-ray photon) and to reduce noise. Thus, a so-called amplifier shaper 206 is preferably used for generating the voltage signal corresponding to the detection events. Further, the read-out electronics comprise two or more pulse discriminators $207_1, \ldots, 207_N$, where each pulse discriminator compares the output signal of the amplifier shaper 206 with a predetermined threshold value $S_i$ (i=1, ..., N) and produces an output signal, if the output of the amplifier shaper exceeds the threshold value $S_i$ (this is also referred to as an event herein below). The threshold values $S_i$ of these pulse discriminators $207_1, \ldots, 207_N$ represent the upper boundaries of the aforementioned energy bins and are selected such that a photon having an energy corresponding to the value of the upper boundary of the energy bin i produces an output of the amplifier shaper 206 that corresponds to the threshold value. The corresponding configuration of the threshold values $S_i$ may be provided within the scope of a calibration procedure of the x-ray device 1, which may be carried out in a way known to the person skilled in the art as such.

As shown in FIG. 2, the output of each comparator $207_1, \ldots, 207_N$ may be connected to an associated counter $208_1, \ldots, 208_N$, which may count the number of events registered in the comparator $207_1, \ldots, 207_N$. For each comparator $207_1, \ldots, 207_N$ or energy bin, the number of events may be provided (in digitalized form) at a readout interface 209 of the radiation detector (along with an indication of the detection location of the events). From the readout interface 209, the event data may be provided to the reconstruction unit 10, which reconstructs the x-ray image of the object using these data. This x-ray image may consists of a set of sub-images, which may include one sub-image for each energy range. Likewise, sub-images for some or all energy ranges may be combined to form a single x-ray image.

One problem often occurring in direct conversion detectors 3 of the aforementioned type are instabilities of the conversion elements 202. Such instabilities are due to charges being trapped within a conversion element 202 to such an extent that they cause the electric field in the conversion element 202 to change. Such changes are also referred to as polarization effect and cause a degradation of the charge collection properties of the respective detector element 201. In particular, polarization may lead to changes in the pulse transient response of the detector and, as a result, the pulse amplitude output by the amplifier shaper 206 may vary for a given photon energy with time and/or photon flux. This effect especially occurs after a sudden change of the incident photon flux and—without correction—it prevents the correct determination of the incident photon flux in such situations. As a result, the generated x-ray image will comprise corresponding artifacts and show a degraded image quality.

In order to correct for the polarization effect and improve image quality, the x-ray device 1 allows for exposing the radiation detector 3 to test radiation pulses and for assessing variations of the output of the radiation detector 3 in response to the exposure of the test radiation pulses. These variations correspond to a measure of the degree of polarization of the radiation detector 3, and on the basis of these variations the reconstruction unit 10 may apply corrections when generating the x-ray image of the object and/or the configuration of the radiation detector 3 may be adapted in order to compensate for the polarization effect. More specifically, individual test radiation pulses or sets of test radiation pulses may be applied to the radiation detector 3 in predetermined time intervals, which are also referred to as observation cycles herein. These radiation pulses or sets of radiation pulses may be configured essentially identically (i.e. the configuration of the radiation emitter is essentially identical when emitting the radiation pulses) so that also the output signals resulting from the detection of these radiation pulses or pulse sequences would be essentially identical without the polarization effect. A variation of the output signals resulting from the detection of different test radiation pulses or pulse sequences therefore allows to assess the polarization of the radiation detector 3 and to provide corresponding corrections in the process of reconstructing x-ray images or adaptations of the detector configuration.

When carrying out a CT scan by means of the x-ray device 1, one observations cycle may correspond to one or plural frame(s) (where one frame corresponds to the period for acquiring one projection as explained above). When each observation cycle corresponds to one frame, the polarization effect can be assessed with a relatively fine time resolution. However, this does also require a relatively fast processing of the electric signals produced by the test radiation pulses. In particular, a relatively fast analog-to-digital conversion for digitizing the amplitude values of the electric pulse signals resulting from the test radiation pulses is required in this implementation. Particularly in view of this requirement and in view of the fact that detector polarization usually evolves on larger time scales compared with a frame period, each observation cycle may correspond to plural frames.

The test radiation pulses are generated by means of one or more radiation source(s) 11, which is/are provided in addition to the x-ray source 2. In one implementation, the radiation source(s) 11 are controlled by the control unit 9 of the x-ray device 1, which may particularly initiate the emission of the test radiation pulses at certain points in time. Further, the control unit 9 may control the configuration of the radiation source(s) 11 used for emitting the radiation pulses, where such configuration particularly includes the settings of the radiation source(s) 11 with respect to the radiation intensity, the wavelength and the duration of the test radiation pulses. In further embodiments, the radiation source(s) 11 may be controlled by other components of the x-ray device 1, such as for example one or more dedicated controller(s) associated with the radiation source(s) 11.

In one embodiment, the test radiation pulses may be laser pulses and each radiation source 11 may be configured as a laser device, such as for example a laser diode. Such laser diodes are relatively compact so that radiation sources 11 configured as laser diodes can easily be integrated into the x-ray device 1. However, it is likewise possible to use other test radiation pulses. Further related examples include light emitted by LEDs and radioactive radiation, which may be provided by means of a controllable radioactive source.

Preferably, the radiation source(s) 11 are located in the area of the radiation detector 3 so that radiation emitted by the radiation source(s) 11 can travel unimpeded to the detector elements 201 of the radiation detector 3. Moreover, corrections and/or adaptations on the basis of the test radiation pulses are preferably carried out individually for each anode pixel 205 of the radiation detector 3. Hereby, account can be taken of the fact that polarization is local effect which may affect the individual anode pixels 205 to a different extent. Therefore, the radiation source(s) 11 is/are preferably configured in such a way that all anode pixels 205 can be exposed to the test radiation pulses.

In principle, the test radiation pulses can be applied to the detector elements 201 of the radiation detector 3 from any direction. So, the test radiation pulses may be applied from the side of the radiation detector 3, i.e. via the face sides of the detector elements 201. In order to apply the test radiation pulses in such a way, there may particularly be one radiation emitter for each row or column of anode pixels 205 of one detector element 201, which emits radiation in the row or column direction. In this case, the radiation intensity will decrease with increasing distance from the radiation emitter due to the absorption of radiation travelling through the conversion element 202.

In further embodiments, the test radiation pulses enter into the conversion element 202 from the top side, i.e. through the cathode contact 203, or from the bottom side, i.e. through the pixelated anode assembly 204. In case the test radiation is applied from the cathode side, the cathode contact 203 may consist of a material which is transparent for the radiation emitted by the radiation source 11, such as, for example, indium tin oxide (ITO) which is transparent in the visible part of the optical spectrum (thus, ITO may be used when the radiation source 11 emits in the visible part of the optical spectrum, which does not necessarily have to be the case, though). As an alternative, the cathode contact 203 may be provided with a small hole for each anode pixel 206, and the test radiation pulse may enter the conversion element 202 via these holes.

Figure 3:
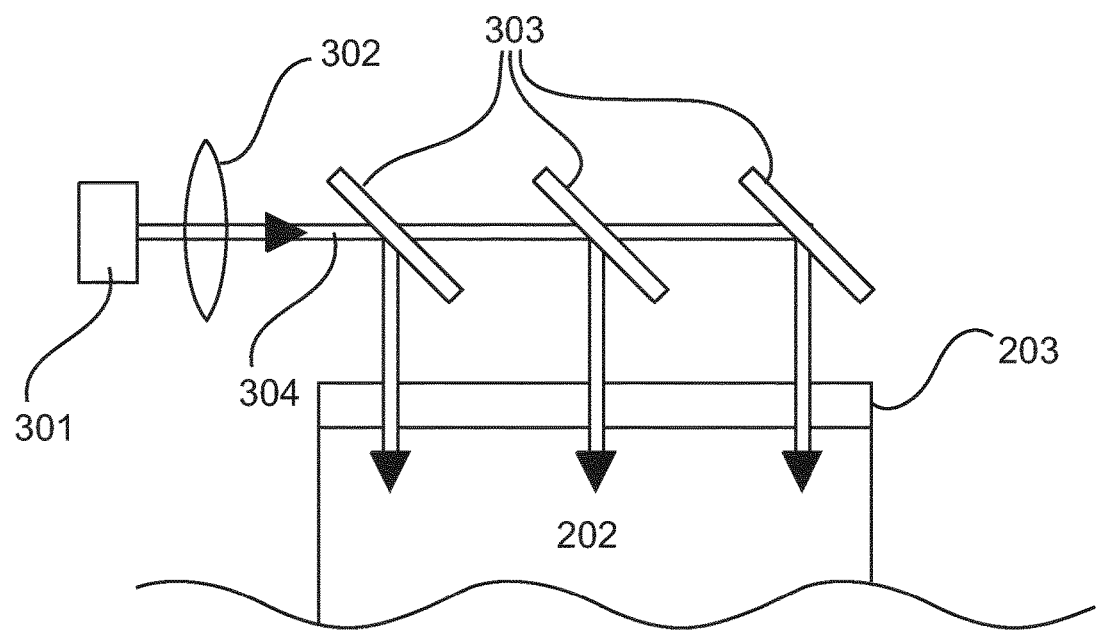

In one implementation of these embodiments, which is schematically and exemplarily illustrated in FIG. 3, the radiation source 11 includes one radiation emitter 301, which may be configured as a laser diode, for each row or column of anode pixels 205 of a detector element 201. The radiation emitter 301 emits the test radiation pulses in the direction of the associated row or column. In order to shape the radiation beam emitted by the radiation emitter, a corresponding optic 302 may be provided in the optical path of the radiation beam 304. Further, beam splitters 303 are provided in the optical path of the radiation beam 304, where one beam splitter is assigned to each anode pixel 205 of the row or column. For each anode pixel 205, the associated beam splitter 303 is configured and arranged in such a way that a part of the radiation beam 304 traverses the beam splitter 303, while another part of the radiation beam 304 is deflected to enter the conversion element 202 in the area of the respective anode pixel 205. In one embodiment, the arrangement is configured such that substantially equal radiation intensities enter the different anode pixels 205. For this purpose, the beam splitters 303 may have different splitting ratios. One exemplary beam splitter 205 which may be used in this implementation is the Pellicle Beamsplitter offered by Newport Corporation.

Using such an arrangement of a radiation emitter 301 and beam splitters 303, the test radiation may be applied to a row or column of anode pixels 205 from the top side (i.e. the cathode side) of the converter element 202 as shown in FIG. 3. However, it is likewise possible to use a similar arrangement to apply the test radiation from the bottom side (i.e. the anode side) of the converter element 202.

In order to assess variations of the outputs of the amplifier shaper 206 resulting from the exposure to the test radiation pulses, these outputs are preferably identified and distinguished from the outputs of the amplifier shaper 206 resulting from x-ray photons incident onto the radiation detector 3. In order to identify the outputs resulting from incident test radiation pulses during the normal operation of the x-ray device 1 several options are provided, which will be described in the following.

In one embodiment, the test radiation pulses are configured such that the output signals of the amplifier shaper 206 resulting from an incident radiation pulse has a higher amplitude (i.e. height) than the output signals resulting from incident x-ray photons. This may be achieved by a suitable selection of the wavelength, intensity and duration of the test radiation pulses. In this embodiment, the output signal resulting from the incident test radiation pulse may be identified as the highest output signal of the amplifier shaper 206 observed during each observation cycle. In this embodiment, one test radiation pulse may be emitted in each observations cycle, and the radiation pulses emitted in different observation cycles may be configured essentially identical. In particular, the radiation pulses may have essentially the same wavelength, intensity and duration.

In one implementation of this embodiment, the output signals of the amplifier shaper 206 are processed in a peak and hold circuit 210 as illustrated in FIG. 2. Such a circuit, which is known to the person skilled in the art as such, monitors the output signals of the amplifier shaper 206 and retains their maximum amplitude as its own output signal. In case the test radiation pulses result in output signals having a higher amplitude than the output signals resulting from incident x-ray photons as described above, the output of the peak and hold circuit 210 at the end of each observation cycle thus corresponds to the amplitude of the output signal resulting from the test radiation pulse at the end of each observation cycle. Therefore, the output signal of the peak and hold circuit 210 observed at the end of each observation cycle may be converted into a digital signal and may particularly be provided at the digital readout interface 209 of the radiation detector 3. For this purpose, the output of the peak and hold circuit 210 may be connected to an analog-to-digital converter (ADC) 211, which may be configured to digitize the output signal of the peak and hold circuit 210 at the end of each observation cycle. After digitization of the output signal of the peak and hold circuit 210, the peak and hold circuit 210 may be reset (so that its output signal is zero again at the beginning of the new cycle). The reset procedure may be controlled by the ADC 211 as illustrated in FIG. 2, or by another component.

Figure 4:
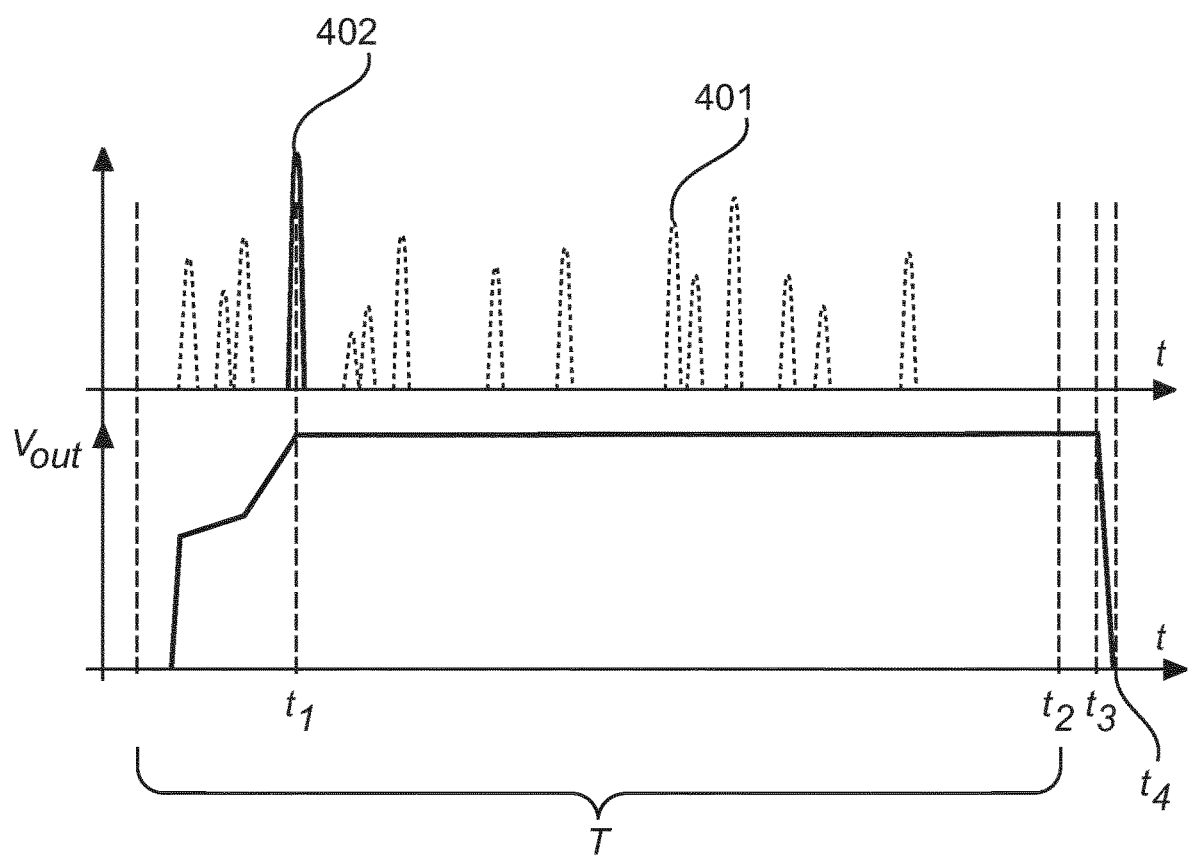

The operation of the peak and hold circuit 210 used in this implementation is further illustrated in FIG. 4. In the upper area, this figure exemplarily and schematically illustrates output pulses 401 (shown in dashed lines) of the amplifier shaper 206 resulting from incident x-ray photons as a function of time t during one observation cycle of duration T. These pulses 401 have different amplitudes in accordance with the different energies of the x-ray photons incident onto the detector element 201. In addition, FIG. 4 shows a pulse signal 402 resulting from the detection of a test radiation pulse. As explained above. This pulse signal 402 has a higher amplitude than the pulse signals corresponding to the x-ray photons so that it can be distinguished from these signals.

In the lower area, FIG. 4 schematically illustrates the output voltage signal $V_{out}$ of the peak and hold circuit as a function of time. As can be seen in the figure, the signal is zero at the beginning of the observation cycle, and increases each time a signal with a higher amplitude than the preceding signals is registered. The maximum output value is reached upon registration of the pulse signal 402 corresponding to the test radiation pulse at the time $t_1$. Upon the expiration of the observation cycle, i.e. from the time $t_2$ to the time $t_3$, the output signal is digitized in the ADC 211. Thereupon, i.e. between the time $t_3$ and the time $t_4$, the peak and hold circuit 210 is reset to output a zero voltage signal.

The analog-to-digital conversion of the amplitude detected in one observation cycle and the subsequent procedure for resetting the peak and hold circuit 210 may be carried out at the beginning of the next observation cycle as shown in FIG. 4. In this case, the time $t_1$ for emitting the test radiation pulse may be selected such that there is a sufficient period of time at the beginning of the observation cycle to perform the analog-to-digital conversion and to carry out the reset procedure. As an alternative, the analog-to-digital conversion and the reset procedure may be carried out after emission of the test radiation pulse in the same observation cycle.

In conclusion, the radiation detector 3 according to the present embodiment provides for each anode pixel 205 and for each observation cycle the determined amplitudes of the output signals resulting from the detection of the test radiation pulses. These data may be used by the reconstruction unit 10 to reconstruct the x-ray image on the basis of these data. In so doing, the reconstruction unit 10 may particularly compare for each anode pixel 205 and for each observations cycle the amplitude of the test radiation pulse 402 with the amplitude of a reference test radiation pulse 402 (also referred to as reference pulse amplitude herein below) and may apply corrections to the x-ray event data acquired during the respective observation cycle on the basis of the result of this comparison.

In general, the reference test radiation pulse may be applied at the time of performing the energy calibration of the radiation detector, which includes the selection of the threshold values differentiating the energy bins. Such an energy calibration may be made in certain time intervals, during which plural x-ray scans may be carried out, or it may be made prior to each x-ray scan. In both cases, the reference test radiation pulse may be applied and the corresponding reference pulse amplitude may be measured after the energy calibration has been made and in a short time distance to the energy calibration so that the measurement reflects the charge collection properties of the radiation detector on the basis of which the energy calibration is carried out. Then, the reference pulse amplitude may be stored for a later use during the x-ray scan. The x-ray source 2 may be switched off and no x-ray radiation may enter the radiation detector 3, when the reference test radiation pulse is applied. Further— particularly in case an energy calibration is carried out prior to each x-ray scan—the reference test radiation pulse 402 may also correspond to the test radiation pulse emitted in the first observation cycle of the x-ray scan.

In order to apply the aforementioned corrections in the process of reconstructing the x-ray image, the reconstruction unit 10 may particularly determine whether the difference between the observed amplitude of the detector output resulting from a the test radiation pulse during an observation cycle and the reference pulse amplitude indicates an incorrect allocation of detected x-ray photons to the energy bins. If the reconstruction unit 10 determines such an indication, it may modify the count numbers for the energy bins accordingly for the respect anode pixel 205.

In one corresponding implementation, the reconstruction unit 10 may calculate a correction parameter or a correction function based on the comparison between the reference pulse amplitude and the observed amplitude resulting from the test radiation pulse for each observation cycle and may perform the reconstruction of the x-ray image using modified energy ranges for the measured x-ray photon events, which are calculated on the basis of the correction parameter. A correction parameter may correspond to a ratio or difference between the reference pulse amplitude and the observed amplitude resulting from the test radiation pulse, and the modified energy ranges may be calculated by shifting the original energy ranges (i.e. the energy ranges on the basis of which the calibration of the x-ray device has been carried out) on the basis of the difference or by multiplying the threshold values defining the energy ranges with the calculated ratio to thereby re-scale the energy thresholds. In case plural test radiation pulses are evaluated, the reconstruction unit 10 may calculate a correction function on the basis of the difference between the pulse amplitudes measured for the test radiation pulses and the corresponding reference pulse amplitudes, for example. The correction may correspond to a first order function or (in case more than two test radiation pulses are evaluated) to a higher order correction function and may be generated by fitting such a function to the differences of the pulse amplitudes. The latter approach using a correction function allows for a more accurate correction of the polarization effect, particularly in case the energy ranges have to be scaled and shifted in order to correct the influence of the polarization.

In addition or as an alternative to such corrections made in the reconstruction unit 10, the configuration of the radiation detector 3 may be adapted in order to compensate for the polarization effect. For this purpose, the determined amplitudes of the output signals resulting from the detection of the test radiation pulses may again be evaluated, and the configuration of radiation detector 3 may be adapted on the basis of these data. This adaption may be made on-the-fly. In this regard, the configuration of the radiation detector 3 may be adapted in one observation cycle on the basis of the data pertaining to the directly preceding observation cycle.

The adaptations of the radiation detector 3 may particularly comprise an adaptation of the gain of the amplifier shaper 206 associated to an anode pixel 205 or an adaptation of the threshold values defining the energy bins for the anode pixel 205. Such modifications may particularly again be made on the basis of the ratio between the reference pulse amplitude and the amplitude resulting from the test radiation pulse observed for the respective anode pixel 205. The adaptation of the threshold values may particularly be made analogue to the modifications of the energy ranges in the reconstruction unit 10.

In one embodiment, such adaptations of the configuration of the radiation detector 3 may be controlled by the control unit 9, which may receive and evaluate the determined amplitudes measured for the test radiation pulses for this purpose. Alternatively, the read-out electronics of the radiation detector 3 may comprise logic for evaluating these amplitudes and controlling the adaptations.

Optionally, a new energy calibration may also be initiated on the basis of the comparison of the observed amplitude of the detector output resulting from a the test radiation pulse during an observation cycle and the reference pulse amplitude in case the difference between these pulse amplitudes becomes too large. For this purpose, the difference or ratio between these pulse amplitudes may be compared with a predetermined threshold in the control unit 9, in the reconstruction unit 10 or by the read-out electronics. If it is determined in this comparison that the difference is too large (e.g. when the difference or ratio exceeds the predetermined threshold), an indication that a new energy calibration should be carried out may be output to an operator of the x-ray device 1.

In a variant of the aforementioned embodiment, each observation cycle is divided into two or more sub-cycles, and in each sub-cycle an individual test radiation pulse is emitted which differs from the test radiation pulse(s) emitted in the other sub-cycle(s). Here, each sub-cycle may correspond to one frame, when the x-ray device 1 performs a CT scan, or each sub-cycle may correspond to a plurality of frames. Thus, when M different test radiation pulses are used, these test radiation pulses may be distributed over M or more frames.

Also in this variant, all radiation pulses are again configured such that the amplitudes of the output signals of the amplifier shaper 206 resulting from these radiation pulses are higher than the amplitudes of the output signals resulting from incident x-ray photons. Thus, the amplitudes of the pulse signals corresponding to the test radiation pulses can be identified in the way described above. However, the test radiation pulses of different sub-cycles may differ in their pulse durations, intensities and/or wavelengths. This allows for assessing the polarization effect under different conditions.

In different observations cycles, the test radiations pulses of corresponding sub-cycles may be essentially identically configured. Thus, if there are N sub-cycles, the test radiation pulses of the i-th sub-cycles of all observation cycles may be essentially identical for i=1, . . . , N. When observed pulse amplitude values corresponding to the test radiation pulses are evaluated in the reconstruction unit 10 and/or in the control unit 9 in order to apply corrections and/or adaptations as explained above, the pulse amplitude value measured for a sub-cycle of one observations cycle may be compared with a corresponding reference amplitude value. This reference amplitude value may correspond to the amplitude value measured in the corresponding sub-cycle of the first observations cycle or may be measured before carrying out the actual x-ray scan as explained above. The comparison may be made for each sub-cycle of an observation cycle so that for each sub-cycle a comparison result is determined. Then, the corrections and/or adaptations may be applied on the basis these comparison results. For this purpose, a correction parameter or function may be determined from the comparison results, and the corrections and/or adaptations may be made based on the correction parameter or function. For example, a correction parameter may correspond to a mean, minimum or maximum of the individual comparison results. A correction function may be generated on the basis of the amplitude differences in a predetermined order. For instance, a first or higher order correction function may be generated on the basis of these differences by fitting such a function to the observed differences as already explained above.

In further embodiments, the output signals of the amplifier shaper 206 resulting from test radiation pulses are not distinguished from output signals resulting from incident x-ray photons on the basis of the signal amplitudes. Rather, the emission of x-ray radiation by the x-ray source 2 is interrupted for short switch-off periods in these embodiments, and the test radiation pulses are emitted and measured during these switch-off periods. As the test radiation pulses constitute the only radiation incident onto the radiation detector 3 during the switch-off periods, it is possible to identify the output signals resulting from the test pulses. It is one advantage of these embodiments that the test radiation pulses do not have to be configured such that the output signals of the amplifier shaper 206 resulting from the test radiation pulses have a higher amplitude than the output signals resulting from incident photons. This also allows for assessing the polarization effect in a wider pulse-height spectrum. Moreover, a pile-up of test radiation pulses and x-ray photons can be prevented, which may occur when the test radiation pulses are applied while the radiation detector 3 is exposed to x-ray radiation. Such a pile-up occurs when the test radiation pulse enters into a detector element 201 concurrently with an x-ray photon and may lead to an incorrect estimation of the polarization of the radiation detector 3.

The switch-off periods in these embodiments may have a short duration of about some microseconds, for example. In order to interrupt the emission of x-ray radiation during the switch-off periods, the x-ray source 2 may be configured as a so-called grid-controlled x-ray tube in these embodiments since such x-ray tubes allow for a fast switching of the emission of x-ray radiation.

For determining the amplitudes of the output signals of the amplifier shaper 206 resulting from the test radiation pulses, a peak and hold circuit 210 may be used for each anode pixel 205 of the radiation detector 3 similar to the embodiments explained above and illustrated in FIG. 2. However, at least in case these amplitudes are not higher than the amplitudes of output signals resulting from incident x-ray photons, the peak and hold circuits 210 are preferably only activated during the switch-off periods. For example, this may be achieved by providing a switch at the input of each peak and hold circuit 210, which allows the output signal of the amplifier shaper 206 to pass to the peak and hold circuit 210 only during the switch-off periods. The corresponding control of the peak and hold circuits 210 or switches may be made by the control unit 9, which may concurrently also control the x-ray source 2 to interrupt the emission of x-ray radiation during the switch-off periods.

Figure 5:
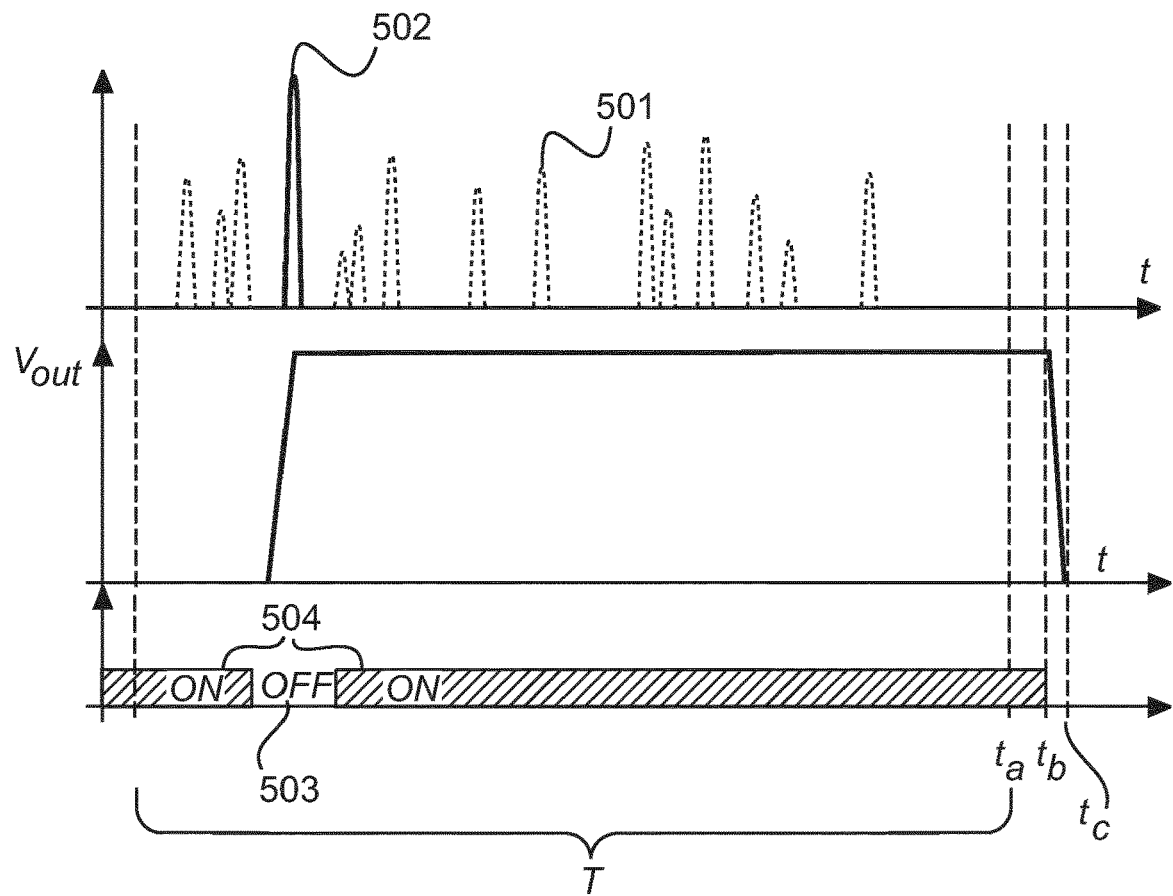

The operation of one peak and hold circuit 210 and the x-ray source 2 in a corresponding embodiment is further illustrated in FIG. 5. In the upper area, this figure exemplarily and schematically illustrates output pulses 501 (shown in dashed lines) of the amplifier shaper 206 resulting from incident x-ray photons as a function of time t during one observation cycle of duration T. In addition, FIG. 5 shows a pulse signal 502 resulting from the detection of a test radiation pulse. The pulse signal 502 shown in FIG. 5 by way of example has a higher amplitude than the output pulses 501 resulting from incident x-ray photons. However, as explained above, this does not necessarily have to be the case, and the amplitude of the pulse signal 502 may likewise be lower than the highest amplitude of the pulse signals 502 corresponding to x-ray photon events.

In the bottom area, FIG. 5 schematically indicates the switch-off period 503 during which the x-ray source 2 does not emit x-ray radiation, and the periods 504 of the observation cycle during which x-ray radiation is emitted by the x-ray source 2. Further, FIG. 5 exemplarily shows the output voltage $V_{out}$ of the peak and hold circuit 201, which is only activated during the switch-off period in the illustrated embodiment. Therefore, the peak and hold circuit 210 does only measure the amplitude of the pulse signal 502 resulting from the test radiation pulse. The output signal of the peak and hold circuit 210 may again be digitized (between the times $t_a$ and $t_b$) and the peak and hold circuit 210 may again be reset (between the times $t_b$ and $t_c$) at the beginning of the next observation cycle as shown in FIG. 5 or at within the observation cycle after expiry of the switch-off period.

The amplitudes of the output signals resulting from the test radiation pulses and determined in such a way are again processed in a way described above in order to apply corrections when reconstructing the x-ray image of the object in the reconstruction unit 10 and/or to adapt the configuration of the radiation detector 3 to compensate for the polarization of the radiation detector 3.

Similar to the embodiments described above, in which the electric pulse signals resulting from incident test radiation pulses are identified on the basis of their amplitude, also the aforementioned embodiments may be varied such that test radiation pulses emitted in accordance with different configurations of the radiation source(s) 11 are used for assessing detector polarization. In particular, each observation cycle may again be divided into sub-cycles as explained above and the configuration of the test radiation pulses may differ for the individual sub-cycles in terms of their intensity, wavelength and/or duration. These test radiation pulses may be measured using the peak and hold circuit 210 as described above and the reconstruction unit 10 and/or the control unit 9 preferably compares the measured signal amplitudes for test radiation pulses emitted in accordance with the same configuration of the radiation source(s) 11 in order to determine one or more correction parameter(s) or function(s) for applying corrections in the process of reconstructing the x-ray image or to modify the configuration of the radiation detector 3.

It is likewise possible to configure the test radiation pulses in such a way that the amplitudes of the pulse signals output by the amplifier shaper 206 in response to incident radiation pulses correspond to the amplitudes of the pulse signals generated in response to incident x-ray photons of different energies. Therefore, correction parameters (e.g. ratios between the amplitudes observed for the test radiation pulses and reference amplitudes as explained above) may be individually calculated for x-ray photon events in each energy bin or range on the basis of a comparison of the pulse amplitudes observed for test radiation impulses of one particular configuration, i.e. test radiation impulses emitted in one of the sub-cycles. In particular, the correction parameter for x-ray photon events in a certain energy bin may be calculated using the measurement for the test radiation pulse producing an output signal of the amplifier shaper 206, which has an amplitude allocated to the energy bin, and on the basis of a comparison of this amplitude with the corresponding reference amplitude. In such a way, it is possible to take account of a possible energy dependence of the polarization effect.

Figure 6:
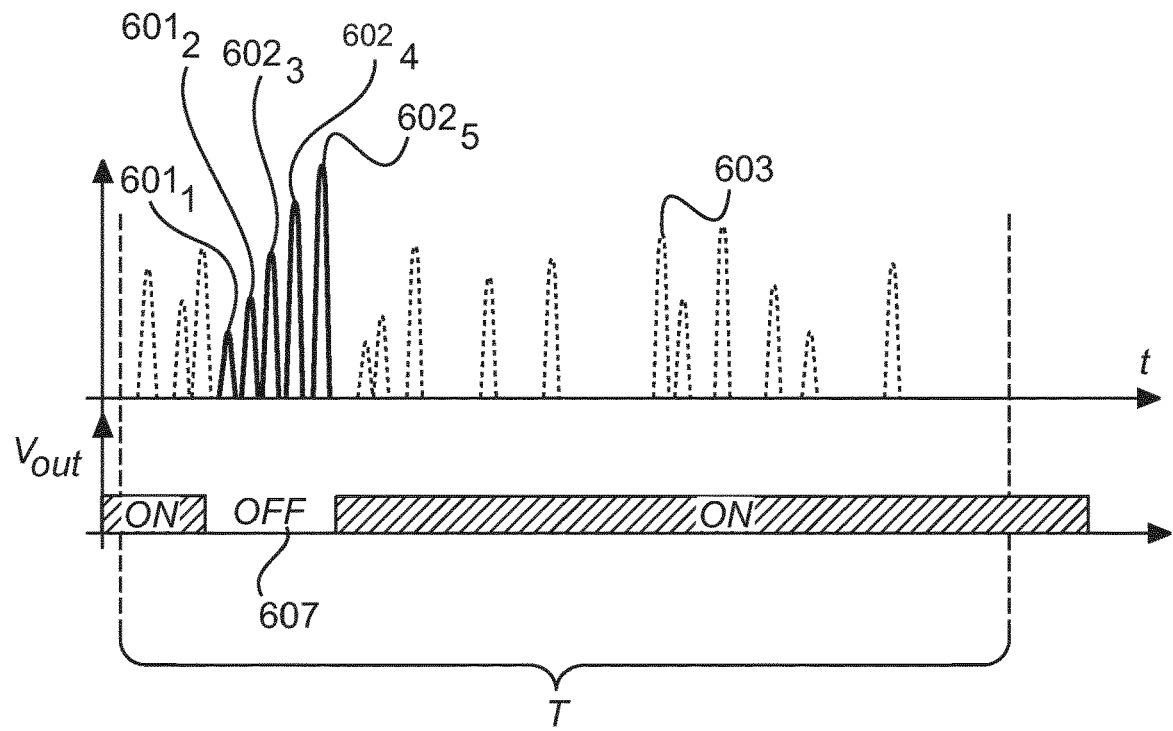

In a further variation, the test radiation pulses emitted in accordance with the different configurations of the radiation source(s) 11 are applied in a single switch-off period in each observation cycle. This is illustrated in FIG. 6, which shows by way of example five different test radiation pulses $601_1, \ldots, 601_5$ (shown in solid lines) which are emitted during a switch-off period 602 within an observation cycle of duration T. For the remaining time of the observation cycle, the radiation detector receives and detects the x-ray radiation as illustrated by the exemplarily pulse signals 603 (shown in dashed lines) in the figure.

In this implementation, the amplitude of the pulse signals resulting from the different test radiation pulses are preferably determined using plural peak and hold circuits 210 instead of the single peak and hold circuit used in the embodiments described above; in particular, one peak and hold circuit may be used for each test radiation pulse so that each peak and hold circuit is assigned to one test radiation pulse. These peak and hold circuits may be configured as separate components, or they may be integrated into a single device (e.g. by providing the device with plural capacitors usually used for sampling the input signal).

The different peak and hold circuits are synchronized with the radiation emitters for emitting the test radiation pulses to be measured. The synchronization may be made in such a way that each peak and hold circuit is deactivated by means of an external signal after the emission of the test radiation pulse assigned to the peak and hold circuit and prior to the emission of the next test radiation pulse. Further, all peak and hold circuits may be activated at the beginning of the switch-off circuit. This may particularly be the case, if the amplitudes of the pulse signals resulting from the test radiation pulses are increasing as shown in FIG. 6. Alternatively, each peak and hold circuit may be activated before the test radiation pulse assigned to the peak and hold circuit is emitted and after the preceding test radiation pulse has been emitted. In the latter case, each peak and hold circuit may also deactivate itself, when it detects that the input signal falls below the maximum value hold in the circuit, so that an external deactivation signal can be dispensed with.

The evaluation of the pulse amplitudes determined for the different test radiation pulses in such way may be made in an analogue way as in the embodiments described before. This does particularly mean that the amplitudes determined in each observations cycle are compared with reference amplitudes resulting from test radiation pulses emitted in accordance with the same configurations of the radiation emitter and that corrections are applied in the process of reconstructing the x-ray image and/or changes are made to the configuration of the radiation detector 3 and the basis of the result of the comparison.

Further embodiments differ from the embodiments described so far in that the emission of the radiation pulses is not made in accordance with a predetermined schedule. In such embodiments, each anode pixel 205 of the radiation detector 3 may be provided with an associated radiation emitter and the radiation emitter may emit test radiation pulses when the readout electronics is not processing an x-ray photon event. In order to achieve that, the read out electronics of an anode pixel 205 may control the radiation emitter assigned to the anode pixel 205 to emit a test radiation pulse when it determines that the pulse signal produced by the amplifier shaper 206 in response to an incident x-ray photon falls below a predetermined threshold.

The radiation emitters used in such embodiments may be configured as laser diodes which are integrated into the CMOS structure forming the read-out electronics, for example. In order to determine the amplitudes of the electric signals produced in response to the incident test radiation pulses, peak and hold circuits may again be used and these circuits may be operated (i.e. activated and deactivated) synchronously to the emission of the test radiation pulses in these embodiments. The evaluation of the determined amplitudes be then made analogue to the embodiments described above.

Further variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention claimed is:

1. An x-ray device for generating an x-ray image of an object, comprising:
   an x-ray radiation source configured to emit x-ray photons;
   a photon-counting radiation detector comprising a plurality of detector elements, each detector element comprising a direct conversion semiconductor material, the radiation detector being configured to convert the x-ray photons having traversed the object into electric pulse signals corresponding to x-ray photon events during an acquisition of the x-ray image;
   a further radiation source configured to expose the radiation detector to a first radiation pulse and during an acquisition of the x-ray image to a second radiation pulse, the first and second radiation pulses being emitted in accordance with a same configuration of the further radiation source; and
   a detection circuit configured to detect a first electric pulse signal generated by the radiation detector in response to the first radiation pulse and a second electric pulse signal generated by the radiation detector in response to the second radiation pulse, wherein the x-ray device is configured to compare amplitudes of the first and second electric pulse signals and generate the x-ray image based on a result of the comparison.

2. The x-ray device defined in claim 1, wherein the further radiation source is controllable to expose the radiation detector to the first radiation pulse prior to or at the beginning of the acquisition of the image.

3. The x-ray device as defined in claim 1, wherein the detection circuit comprises a peak and hold circuit for determining the amplitude of the second electric pulse signal.

4. The x-ray device as defined in claim 1, wherein the configuration of the further radiation source is selectable such that an amplitude of the first and second electric pulse signals is higher than amplitudes of electric pulse signals generated by the radiation detector in response to an exposure to x-ray radiation, and wherein the detection circuit is configured to identify an electric pulse signal generated by the radiation detector, which has the highest amplitude during an acquisition period, as the second electric pulse signal.

5. The x-ray device as defined in claim 1, wherein the further radiation source is controllable to expose the radiation detector to the first and/or second radiation pulses in a time period in which the emission of x-ray radiation by the x-ray radiation source is interrupted.

6. The x-ray device as defined in claim 5, wherein the detection circuit comprises a peak and hold circuit for determining the amplitude of the second electric pulse signal and wherein the peak and hold circuit is controllable such that it is only activated while the x-ray radiation source does not emit x-ray radiation.

7. The x-ray device as defined in claim 1, wherein
the further radiation source is configured to expose the radiation detector to at least two first radiation pulses emitted in accordance with different configurations of the further radiation source and to at least two second radiation pulses, each second radiation pulse being emitted in accordance with one of said configurations of the further radiation source,
for each second radiation pulse emitted in accordance with one of the configurations of the further radiation source, the x-ray device is configured to compare the amplitude of the electric pulse signal generated in response to the exposure of the radiation detector to the respective second radiation pulse with the amplitude of the electric pulse signal generated by the radiation detector in response to the exposure to the first radiation pulse emitted in accordance with the same configuration of the further radiation source, and
the x-ray device is further configured to generate the x-ray image based on the results of the comparisons.

8. The x-ray device as defined in claim 7, wherein the further radiation source is controllable to successively emit at least two second radiation pulses in one a time period in which the emission of x-ray radiation by the x-ray radiation source is interrupted.

9. The x-ray device as defined in claim 1, comprising a reconstruction unit configured to reconstruct the x-ray image based on electric pulse signals generated by the radiation detector in response to an exposure to x-ray radiation and based on the result of the comparison between the amplitudes of the first and second electric pulse signals.

10. The x-ray device as defined in claim 9, wherein the radiation detector is configured to allocate an energy range to each of a plurality of x-ray photons entering the radiation detector based on the electric pulse signals generated in response to the entering of the x-ray photons, and wherein the reconstruction unit is configured to modify the allocation for at least some of the x-ray photons based on the result of the comparison between the amplitudes of the first and second electric pulse signals.

11. The x-ray device as defined in claim 1, comprising read-out electronics of the radiation detector, the read-out electronics being configured to process the electric pulse signals generated in response to an exposure to x-ray radiation based on the result of the comparison between the amplitudes of the first and second electric pulse signals.

12. The x-ray device as defined in claim 11, wherein the processing of the electric pulse signals generated in response to an exposure to x-ray radiation includes amplifying the electric pulse signals using a gain selected on the basis of the result of the comparison between the amplitudes first and second electric pulse signals.

13. The x-ray device as defined in claim 11, wherein the processing of the electric pulse signals generated in response to an exposure to x-ray radiation includes allocating energy ranges to the electric pulse signals based on the result of the comparison between the amplitudes of the first and second electric pulse signals.

14. The x-ray device as defined in claim 1, wherein the further radiation source is a laser device, and wherein the first and second radiation pulses comprise laser radiation.

15. A method for generating an x-ray image of an object using a photon-counting radiation detector, the method comprising:
emitting x-ray photons by an x-ray radiation source;
converting, by the radiation detector, the x-ray photons having traversed the object into electric pulse signals corresponding to x-ray photon events during an acquisition of the x-ray image, wherein the radiation detector comprises a plurality of detector elements, each detector element comprising a direct conversion semiconductor material;
exposing the radiation detector to a first radiation pulse emitted by a further radiation source;
obtaining a first electric pulse signal generated by the radiation detector in response to the first radiation pulse;
exposing the radiation detector to a second radiation pulse emitted by the further radiation source during the acquisition of the image;
obtaining a second electric pulse signal generated by the radiation detector in response to the second radiation pulse, wherein the first and second radiation pulses are emitted in accordance with a same configuration of the further radiation source;
comparing amplitudes of the first and second electric pulse signals; and
generating the x-ray image based on a result of the comparison.

* * * * *